(12) United States Patent
Saunders et al.

(10) Patent No.: US 7,432,292 B2
(45) Date of Patent: Oct. 7, 2008

(54) SULFHYDANTOINS AS PHOSPHATE ISOSTERES

(75) Inventors: Jeffrey O. Saunders, Acton, MA (US); Gregory F. Miknis, Broomfield, CO (US); James F. Blake, Longmont, CO (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 338 days.

(21) Appl. No.: 10/749,121

(22) Filed: Dec. 30, 2003

(65) Prior Publication Data

US 2004/0167187 A1 Aug. 26, 2004

Related U.S. Application Data

(60) Provisional application No. 60/437,572, filed on Dec. 30, 2002.

(51) Int. Cl.
*A61K 31/433* (2006.01)
*C07D 285/10* (2006.01)

(52) U.S. Cl. .................................. 514/362; 548/135
(58) Field of Classification Search ................ 548/127; 514/362
See application file for complete search history.

(56) References Cited

U.S. PATENT DOCUMENTS

| | | | |
|---|---|---|---|
| 5,494,925 A | 2/1996 | Court et al. ............... 514/362 |
| 5,512,576 A | 4/1996 | Desai et al. ............... 514/258 |
| 5,541,168 A | 7/1996 | Court et al. ................ 514/92 |
| 5,550,139 A | 8/1996 | Groutas .................... 514/362 |
| 5,556,909 A | 9/1996 | Desai ....................... 514/362 |
| 5,750,546 A | 5/1998 | Desai ....................... 514/342 |
| 2004/0023974 A1* | 2/2004 | Coppola et al. ........ 514/252.05 |

FOREIGN PATENT DOCUMENTS

WO WO 03/082841 A1 10/2003
WO WO 2004050646 A1 * 6/2004

OTHER PUBLICATIONS

Mantegani, et al., "Synthesis and Antihypersensitive Activity of 2,4-Dioxoimidazolidin-1-yl and Perhydro-2,4-Dioxopyrimidin-1-yl Ergoline Derivatives", IL Farmaco, 53 (4): 293-304 (1998).*
Albericio, et al., "Synthesis of a Sulfahydantoin Library", J. Comb. Chem. 2, 290-300 (May 2001).*
Lee, et al., "Intra- and Intermolecular α—Sulfamidoalkylation Reactions", J. Org. Chem. 55(25): 6098-6104 (1990).*
Bright, et al., Journal of Immunological Methods, "Competitive particle concentration fluorescence immunoassays for measuring anti-diabetic drug levels in mouse plasma", vol. 207 (1), pp. 23-31, (1997).*
Mantegani et al., "Synthesis And Antihypertensive Activity Of 2,4-Dioxoimidazolidin-1-yl And Perhydro-2,4-Dioxopyrimidin-1-yl Ergoline Derivatives", IL Farmaco, 53 (4): 293-304 (1998).
Bright et al, "Competitive Particle Concentration Fluorescence Immunoassays For Measuring Anti-Diabetic Drug Levels In Mouse Plasma", Journal of Immunological Methods, 207 (1): 23-31 (1997).
Albericio et al., "Synthesis of a Sulfahydantoin Library", J. Comb. Chem. 3, 290-300 (2001).
Kuang et al., "A General Inhibitor Scaffold for Serine Proteases with a (Chymo)trypsin-Like Fold: Solution-Phase Construction and Evaluation of the First Series of Libraries of Mechanism-Based Inhibitors", J. Am. Chem. Soc. 121 (35): 8128-8129 (1999).
Groutas et al, Potent and Specific Inhibition of Human Leukocyte Elastase, Cathepsin G and Proteinase 3 by Sulfone Derivatives Employing the 1,2,5-Thiadiazolidin-3-one 1,1 Dioxide Scaffold, Bioorganic & Medicinal Chemistry 6 (6): 661-671 (1998).
Groutas et al, "Structure-Based Design of a General Class of Mechanism-Based Inhibitors of the Serine Proteinases Employing a Novel Amino Acid-Derived Heterocyclic Scaffold" Biochemistry, 36(16): 4739-4750 (1997).
Dewynter et al, "Synthesis of Pseudonucleosides Containing Chiral Sulfahydantoins as Aglycone (II)", Tetrahedron , 52 (3): 993-1004 (1996).
Muller et al., "A General Synthesis of 4-Substituted 1, 1-Dioxo-1,2,5-thiadiazolidin-3-ones Derived from alpha Amino Acids", J. Org. Chem., 54 (18): 4471-4473 (1989).
Lee et al, "3-Oxo and 3-Imino-4-substituted-1,2,5-thiadiazolidine 1,1-Dioxides: Synthesis, Spectral Properties, and Selected Chemistry", J. Org. Chem., 54 (13): 3077-3083 (1989).

(Continued)

*Primary Examiner*—Rebecca L Anderson
*Assistant Examiner*—Michael P Barker
(74) *Attorney, Agent, or Firm*—Michael C. Badia

(57) ABSTRACT

The present invention relates to novel phosphate isosteres. The invention relates to compounds having a sulfhydantoin or a reverse sulfhydantoin moiety, uses thereof, and related methods. The present invention relates to compounds of formula I or II:

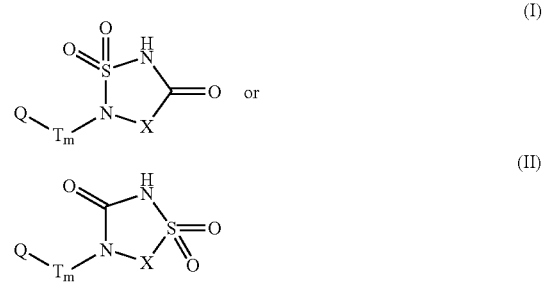

or pharmaceutically acceptable salts thereof; wherein Q, T, m, and X are as described herein. These compounds are inhibitors of phosphatases, particularly inhibitors of SHP-2. The invention also provides pharmaceutically acceptable compositions comprising the compounds of the invention and methods of utilizing these compounds and compositions in the treatment of various phosphatase-mediated diseases.

3 Claims, No Drawings

OTHER PUBLICATIONS

Tremblay et al, "Efficient Solid-Phase Synthesis of Sulfahydantoins", J. Comb. Chem., 4 (5): 429-435 (2002).

Albericio et al, "Solid Phase synthesis of Sulfahydantoins", Tetrahedron Letters, 41 (17) 3161-3163 (2000).

* cited by examiner

SULFHYDANTOINS AS PHOSPHATE ISOSTERES

CROSS-REFERENCE TO RELATED APPLICATIONS

The present application claims the benefit of U.S. application 60/437,572, filed Dec. 30, 2002, the disclosure whereof is incorporated herein by reference.

TECHNICAL FIELD OF THE INVENTION

The present invention relates to novel phosphate isosteres. The invention relates to compounds having a sulfhydantoin or a reverse sulfhydantoin moiety, uses thereof, and related methods.

BACKGROUND OF THE INVENTION

Many biologically important functions are regulated by the transfer of a phosphate group. Often, the active or inactive form of a compound is determined by the presence or absence of a phosphate group bound to that compound. Accordingly, many biological enzymes are involved in regulating this phosphate group transfer. For example, kinase enzymes catalyze transfer of a phosphate group from a nucleoside triphosphate to a protein receptor. In contrast, phosphatase enzymes remove a phosphate group from a substrate by hydrolysis.

SHP-2 (src homology 2-containing protein tyrosine phosphatase) is a 68 kDa phosphatase protein and is also known as SHPTP2, Syp, PTP1D and PTP2C. Lu et al., *Molecular Cell* (2001) 8, 759. The enzyme is expressed in the cytoplasm of every tissue. SHP-2 is an important signaling enzyme, and the biological functions of SHP-2 have been extensively reviewed. Feng, *Exp. Cell Res.* (1999) 253, 45; Neel and Tonks, *Curr. Opin. Cell Biol.* (1997) 9, 193; Tonks, *Adv. Pharmacol.* (1996) 36, 91. The enzyme is activated through interactions with a variety of ligands including growth factors, cytokine receptor tyrosine kinases, and adhesion molecules and is most notably recognized as a positive regulator of cell proliferation. SHP-2 also plays an important function in immune signaling. Huyer and Alexander, *Curr. Biol.* (1999) 9, R129; Cohen et al., *Cell* (1995) 80, 237. The SHP-2 enzyme is required for activation of the Ras-MAP kinase cascade, although its precise role in the pathway is unclear. Van Vactor et al., *Curr. Opin. Genet. Dev.* (1998) 8, 112. SHP-2 has recently been identified as an intracellular target of *Helicobacter pylori*. Higashi et al., *Science* (2002) 295, 683. Due to the critical role SHP-2 plays in various biological pathways, development of inhibitors against the enzyme would provide useful treatments for cancer and other autoimmune diseases.

Development of new chemical entities that modulate phosphatase enzymes such as SHP-2 would be an important advance and could lead to the development of novel treatments for diseases in which phosphatase enzymes play a critical role. The development of phosphatase modulators is an active area of research and has been extensively reviewed. Ripka, *Annual Rev. Med. Chem.* (2000) 35, Chapter 21 and references cited therein.

The majority of compounds investigated to date as potential phosphatase inhibitors can be divided into two general classes. The most common phosphatase inhibitors incorporate one or two carboxylate groups to mimic the two formal negative charges present on phosphate at physiological pH. Another common class of phosphatase inhibitors incorporates the mono- or diflouro phosphinate moiety as a non-hydrolyzable phosphate group mimic.

More recent work has focused on the development of new heterocyclic groups that can mimic a phosphate moiety, i.e. the development of phosphate isosteres. A successful phosphate isostere will ideally be both nonhydrolyzable and bioavailable. Successful phosphate mimicry will also depend on the shape and ionization state of the mimic. Examples of new heterocyclic groups designed to mimic a phosphate moiety include tetronic acid derivatives investigated against Cdc25b, Sodeoka et al., *J. Med. Chem.* (2001) 44(20), 3216, and the azoledinedione class of inhibitors that have been investigated against protein tyrosine phosphatase 1B (PTB1B). Malamas et al., *J. Med. Chem.* (2000) 43, 995. However, the efficacy of these mimics is still being investigated.

Although 2-alkyl sulfhydantoins have been reported as serine protease inhibitors, Groutas et al., *Biochemistry* (1997) 36, 4739; Hlasta et al., *J. Med. Chem.* (1995) 38, 4687, they have never been recognized as phosphate mimics.

There is still a great need to develop potent modulators of phosphatase enzymes and other enzymes that are involved in regulating the transfer of a phosphate group. There is also a need to develop new chemical entities useful as phosphate isosteres.

SUMMARY OF THE INVENTION

The present invention is directed to the discovery that the sulfhydantoin moiety is useful as an isosteric replacement for a phosphate group. The present invention describes the novel use of compounds containing a sulfhydantoin (1,1-dioxo[1,2,5]thiadiazolidin-3-one) or a reverse sulfhydantoin (1,1-dioxo[1,2,4]thiadiazolidin-3-one) ring system as phosphate isosteres. The present invention also describes the use of these compounds as phosphatase enzyme modulators. In particular, it has now been found that compounds of this invention, and pharmaceutically acceptable compositions thereof, are effective as inhibitors of SHP-2 phosphatase enzyme. These compounds have the general formulae (I) and (II):

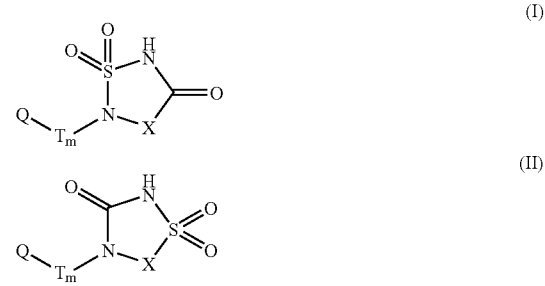

or pharmaceutically acceptable salts thereof, wherein Q, T, m, and X are as described below.

These compounds, and pharmaceutically acceptable compositions comprising them, are useful for treating or reducing the risk of a variety of disorders, such as cancers and autoimmune diseases.

DETAILED DESCRIPTION OF THE INVENTION

The present invention is directed to the discovery that the sulfhydantoin moiety is useful as an isosteric replacement for a phosphate group. The present invention provides compounds of formulae (I) and (II):

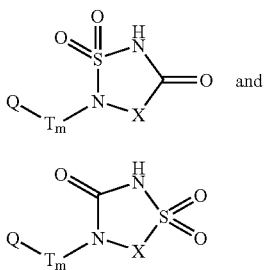

or pharmaceutically acceptable derivatives thereof, wherein:

Q is an optionally substituted group selected from $C_{1-8}$ aliphatic; $C_{6-10}$ aryl, heteroaryl having 5-10 ring atoms, and heterocyclyl having 3-10 ring atoms;

T is selected from a $C_{1-6}$ alkylidene chain wherein one or two non-adjacent methylene units of T are optionally and independently replaced by —O—, —NR—, —S—, —C(O)—, —C(O)NR—, —NRC(O)—, —NRC(O)NR—, —SO—, —SO$_2$—, —NRSO$_2$—, —SO$_2$NR—, or —NRSO$_2$NR—;

m is selected from zero or one;

X is selected from —CH$_2$—, —C(O)—, or —CF$_2$—; and each R is independently selected from hydrogen or an optionally substituted $C_{1-8}$ aliphatic group, or two R groups bound to the same nitrogen are taken together with the nitrogen to form a 3-7 membered heterocyclic ring having 0-2 heteroatoms in addition to the nitrogen, wherein said heteroatoms are independently selected from nitrogen, oxygen, or sulfur.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of any other substitutions.

The term "aliphatic" or "aliphatic group" as used herein means a straight-chain or branched $C_1$-$C_{12}$ hydrocarbon chain that is completely saturated or that contains one or more units of unsaturation, or a monocyclic $C_3$-$C_8$ hydrocarbon, or bicyclic $C_8$-$C_{12}$ hydrocarbon that is completely saturated or that contains one or more units of unsaturation, but which is not aromatic (also referred to herein as a "carbocycle" or "cycloalkyl"), that has a single point of attachment to the rest of the molecule, wherein any individual ring in said bicyclic ring system has 3-7 members. For example, suitable aliphatic groups include, but are not limited to, linear or branched alkyl, alkenyl, and alkynyl groups and hybrids thereof such as (cycloalkyl)alkyl, (cycloalkenyl)alkyl, and (cycloalkyl)alkenyl.

The term "alkylidene chain" means a saturated or unsaturated, straight or branched $C_{1-6}$ carbon chain that is optionally substituted and wherein up to two non-adjacent saturated carbons of the chain are each optionally and independently replaced by —O—, —NR—, —S—, —C(O)—, —C(O) NR—, —NRC(O)—, —NRC(O)NR—, —SO—, —SO$_2$—, —NRSO$_2$—, —SO$_2$NR—, or —NRSO$_2$NR—, wherein R is as described above. Optional substituents on the alkylidene chain are as described below for an aliphatic group.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety include both straight and branched chains containing two to twelve carbon atoms.

The terms "haloalkyl", "haloalkenyl", and "haloalkoxy" mean alkyl, alkenyl, and alkoxy, respectively, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. The term "nitrogen" also includes a substitutable nitrogen of a heterocyclic ring. As an example, in a saturated or partially unsaturated ring having 0-3 heteroatoms selected from oxygen, sulfur, or nitrogen, the nitrogen may be N (as in 3,4-dihydro-2H-pyrrolyl), NH (as in pyrrolidinyl), or NR$^+$ (as in N-substituted pyrrolidinyl).

The term "aryl", used alone or as part of a larger moiety as in "aralkyl", "aralkoxy", or "aryloxyalkyl", refers to monocyclic, bicyclic, and tricyclic carbocyclic ring systems having a total of five to fourteen ring members, wherein at least one ring in the system is aromatic, and wherein each ring in the system contains 3 to 8 ring members. The term "aryl" may be used interchangeably with the term "aryl ring".

The term "heterocycle", "heterocyclyl", or "heterocyclic" as used herein means non-aromatic, monocyclic, bicyclic, or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic, and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl, heteroaryl, aralkyl, or heteroaralkyl group are selected from halogen; haloalkyl; —CF$_3$; —R$^\circ$; —OR$^\circ$; —SR$^\circ$; 1,2-methylene-dioxy; 1,2-ethylenedioxy; protected OH (such as acyloxy); phenyl (Ph); Ph substituted with R$^\circ$; —O(Ph); —O(Ph) substituted with R$^\circ$; —CH$_2$(Ph); —CH$_2$ (Ph) substituted with R$^\circ$; —CH$_2$CH$_2$(Ph); —CH$_2$CH$_2$(Ph) substituted with R$^\circ$; —NO$_2$; —CN; —N(R$^\circ$)$_2$; —NR$^\circ$C(O) R$^\circ$; —NR$^\circ$C(O)N(R$^\circ$)$_2$; —NR$^\circ$CO$_2$R$^\circ$; —NR$^\circ$NR$^\circ$C(O)R$^\circ$; —NR$^\circ$NR$^\circ$C(O)N(R$^\circ$)$_2$; —NR$^\circ$NR$^\circ$CO$_2$R$^\circ$; —C(O)C(O) R$^\circ$; —C(O)CH$_2$C(O)R$^\circ$; —CO$_2$R$^\circ$; —C(O)R$^\circ$; —C(O)N (R$^\circ$)$_2$; —OC(O)N(R$^\circ$)$_2$; —S(O)$_2$R$^\circ$; —SO$_2$N(R$^\circ$)$_2$; —S(O) R$^\circ$; —NR$^\circ$SO$_2$N(R$^\circ$)$_2$; —NR$^\circ$SO$_2$R$^\circ$; —C(=S)N(R$^\circ$)$_2$; —C(=NH)—N(R$^\circ$)$_2$; or —(CH$_2$)$_y$NHC(O)R$^\circ$; wherein each R$^\circ$ is independently selected from hydrogen, an optionally substituted $C_{1-6}$ aliphatic, an unsubstituted 5-6 membered heteroaryl or heterocyclic ring, phenyl (Ph), —O(Ph), or —CH$_2$(Ph)—CH$_2$(Ph); and wherein y is 0-6. When R$^\circ$ is $C_{1-6}$ aliphatic, it may be substituted with one or more substituents selected from —NH$_2$, —NH(C$_{1-4}$ aliphatic), —N(C$_{1-4}$ aliphatic)$_2$, —S(O)(C$_{1-4}$ aliphatic), —SO$_2$(C$_{1-4}$ aliphatic), halogen, —C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or -halo(C$_{14}$ aliphatic), wherein each C$_{1-4}$ aliphatic is unsubstituted.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =NNHC(O)R*, =NNHCO$_2$(C$_{1-14}$ aliphatic), =NNHSO$_2$(C$_{1-4}$ aliphatic), or =NR*, where each R* is independently selected from hydrogen or an optionally substituted C$_{1-6}$ aliphatic. When R* is C$_{1-6}$ aliphatic, it may be substituted with one or more substituents selected from —NH$_2$, —NH(C$_{1-4}$ aliphatic), —N(C$_{1-4}$ aliphatic)$_2$, halogen, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or -halo C$_{1-4}$ aliphatic, wherein each C$_{1-4}$ aliphatic is unsubstituted.

Substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein each R$^+$ is independently selected from hydrogen, an optionally substituted C$_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5-6 membered heteroaryl or heterocyclic ring. When R$^+$ is a C$_{1-6}$ aliphatic group or a phenyl ring, it may be substituted with one or more substituents selected from —NH$_2$, —NH(C$_{1-4}$ aliphatic), —N(C$_{1-4}$ aliphatic)$_2$, halogen, —C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or -halo(C$_{14}$ aliphatic), wherein each C$_{1-4}$ aliphatic is unsubstituted.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C— or $^{14}$C-enriched carbon are within the scope of this invention.

Compounds of this invention may exist in alternative tautomeric forms. Unless otherwise indicated, the representation of either tautomer is meant to include the other.

The term "ligand" as used herein means any molecule that interacts with a protein. Accordingly, the term ligand will be understood to include, without limitation, a substrate of a protein, an agonist of a protein, an antagonist of a protein, and a second protein.

The term "protein:ligand complex" as used herein refers to a ligand bound to a protein.

The term "substrate" as used herein refers to a molecule on which a protein, particularly an enzyme, acts.

The term "mechanistically significant phosphate group" as used herein means a phosphate group in a ligand that is involved in an interaction between the ligand and a protein. Preferably, this interaction is an attractive interaction. More preferably, this interaction is a chemical interaction. For example, the mechanistically significant phosphate group may participate in covalent and/or non-covalent interactions with the protein such as hydrogen bonds, ionic interactions, lipophilic interactions, and steric interactions.

The term "phosphate isostere" or "phosphate mimic" as used herein means a moiety that mimics the role of a mechanistically significant phosphate group in a native ligand of a protein.

The term "sulfhydantoin moiety" or "sulfhydantoin fragment" as used herein means a functional group comprising the formula:

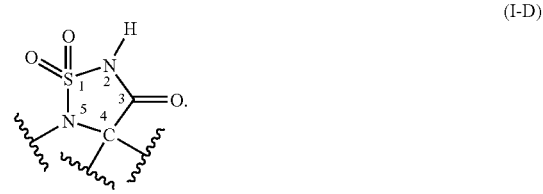

(I-D)

It is understood that the two bonds on C-4 may be to the same atom (e.g., an oxygen) or to two different atoms. One of ordinary skill in the art will recognize that while compounds comprising formula I-D may be substituted at the C-4 and N-5 positions, as indicated by the wavy lines in formula I-D, the presence or absence of non-hydrogen substituents at these positions does not alter the core ring structure that constitutes the essence of the sulfhydantoin moiety. Accordingly, one of ordinary skill in the art will recognize that compounds having a sulfhydantoin moiety or sulfhydantoin fragment are defined by the five-membered heterocyclic 1,1-dioxo[1,2,5]thiadiazolidin-3-one core as in formula I-D, including any substituted variants thereof, so long as such compounds are chemically feasible and stable.

The term "reverse sulfhydantoin moiety" or "reverse sulfhydantoin fragment" as used herein means a functional group comprising the formula:

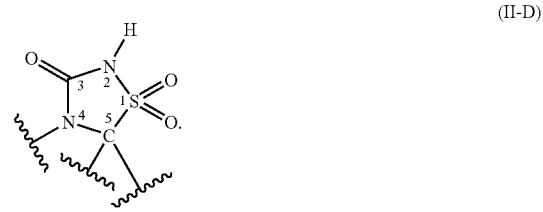

(II-D)

It is understood that the two bonds on C-5 may be to the same atom (e.g., an oxygen) or to two different atoms. One of ordinary skill in the art will recognize that while compounds comprising formula II-D may be substituted at the N-4 and C-5 positions, as indicated by the wavy lines in formula II-D, the presence or absence of non-hydrogen substituents at these positions does not alter the core ring structure that constitutes the essence of the reverse sulfhydantoin moiety. Accordingly, one of ordinary skill in the art will recognize that compounds having a reverse sulfhydantoin moiety or reverse sulfhydantoin fragment are defined by the five-membered 1,1-dioxo[1,2,4]thiadiazolidin-3-one heterocyclic core as in formula II-D, including any substituted variants thereof, so long as such compounds are chemically feasible and stable.

The term "isostere" or "classical isostere" as used herein means a group or molecule whose chemical and physical properties are similar to those of another group or molecule. The term isostere is generally understood to refer to a portion of a molecule, rather than to the entire molecule. Thornber, *Chem. Soc. Rev.* (1979) 8, 563.

The term "bioisostere", "bioisosteric replacement", or "non-classical isostere" as used herein means a group or molecule whose chemical and physical similarities to another group or molecule produce similar biological properties. The term bioisostere is generally understood to refer to a portion of a molecule, rather than to the entire molecule. A bioisostere of a compound may produce a similarity in a biologically important parameter. A bioisostere of a compound may be useful to attenuate toxicity, modify activity, and/or alter the metabolism of the compound. The following parameters may be considered in developing a bioisosteric replacement: size, shape, electronic distribution, lipid solubility, water solubility, $pK_a$, chemical reactivity, and hydrogen bonding capacity, as set forth in Thornber, *Chem. Soc. Rev.* (1979) 8, 563, which is incorporated by reference herein in its entirety.

The term "binding pocket", as used herein, refers to a region of a molecule or molecular complex, that, as a result of its shape, favorably associates with another chemical entity or compound. Those of skill in the art will recognize that the association of natural ligands or substrates with the binding pockets of their corresponding receptors or enzymes is the basis of many biological mechanisms of action. Similarly, many drugs exert their biological effects through association with the binding pockets of receptors and enzymes. Such an association may occur with all or any part of a binding pocket. An understanding of such associations will help lead to the design of drugs having more favorable associations with their target receptor enzyme, and thus, improved biological effects. Therefore, this information is valuable in designing potential ligands or modulators of receptors or enzymes, such as inhibitors of phosphatases, including the serine/threonine phosphatases, the dual-specificity phosphatases, and the phosphotyrosine phosphatases (PTPs), and particularly SHP-2.

The term "associate" is used herein to describe the proximity between chemical entities or compounds, or portions thereof. The association may be non-covalent—wherein the juxtaposition is energetically favored by electrostatic or van der Waals interactions—or it may be covalent.

The present invention is directed to the discovery that the sulfhydantoin moiety or the reverse sulfhydantoin moiety is useful as an isosteric replacement for a phosphate group. Accordingly, one embodiment of this invention relates to a phosphate isostere having the formula:

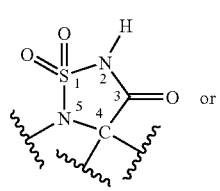

(I-D)

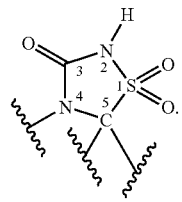

(II-D)

According to a preferred embodiment, the replacement of a mechanistically significant phosphate group within a molecule with a sulfhydantoin moiety or a reverse sulfhydantoin moiety can be represented structurally in Schemes 1 and 2 below, wherein "Molec" represents the remainder of the molecule comprising the mechanistically significant phosphate group:

Scheme 1

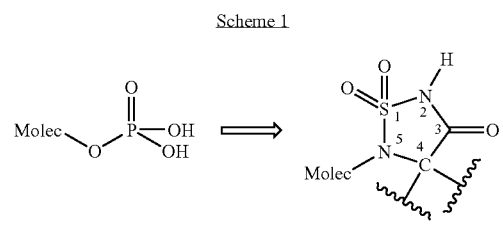

Isosteric replacement of phosphate with sulfhydantoin moiety.

Scheme 2

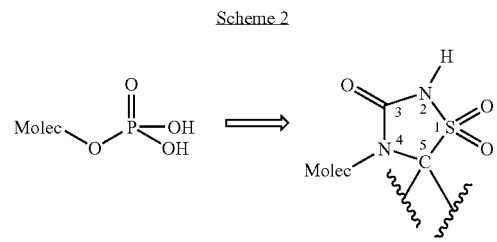

Isosteric replacement of phosphate with reverse sulfhydantoin moiety

According to a preferred embodiment, the phosphate isostere is a phosphate bioisostere.

One embodiment of the present invention relates to a method of using a compound comprising a sulfhydantoin moiety or a reverse sulfhydantoin moiety as a phosphate isostere comprising the step of contacting said compound with a protein, wherein a natural ligand of the protein comprises at least one mechanistically significant phosphate group. Preferably, the protein is an enzyme. Preferably, the enzyme is a binding domain for the natural ligand. More preferably, the binding domain is a receptor for the natural ligand.

In a preferred embodiment, the protein is selected from the group consisting of phosphatase; kinase; nucleotidase; SH2 domains; dehydrogenases, oxidase, reductases, and other NAD-dependent proteins or flavin-dependent proteins; RNA and DNA helicases; RNA and DNA polymerases; sodium/potassium ATPase (proton pump); P-type cation transport ATPases; carboxykinase; ATP synthase; ATP-dependent proteases; phosphotransferases; phosphoribosyltransferase; myosins, kinesins, and other motor proteins; dynamins and dynamin-like proteins; ADP-ribosylation factors; DNA repair proteins; RNA splicing proteins; DNA ligases; coenzyme A-dependent enzymes; acyl carrier protein phosphopantetheine domains; citrate lyases; thiamine pyrophosphate-dependent proteins; phosphodiesterases; RNA cyclases; carbamoyl-phosphate synthases; glucosamine-6-phosphate isomerase; triosephosphate isomerase; ribulose-phosphate 3-epimerase; pyridoxal-phosphate-dependent proteins; cAMP- and cGMP-dependent proteins; PID (phosphotyrosine-interacting domain) proteins; phospholipases; phosphatidylethanolamine-binding protein; PH domains; phospholipid-binding proteins; phosphate-dependent receptors; inositol phosphate-binding proteins; phosphotyrosine-binding proteins; phosphoserine-binding proteins; phosphohistidine-binding proteins; phosphate-dependent transcriptional regulators; phosphate-dependent transporters; sulfate-dependent transporters; NTPases; DNA replication proteins; nucleotide-sugar transferases; phosphorylases; sugar phosphotransferases; sulfatases; nucleases; and arrestins. Preferably, the protein is a phosphatase. More preferably, the phosphatase is SHP-2.

In another preferred embodiment, the natural ligand is a substrate of the protein. In another preferred embodiment, the natural ligand is a second protein. In still another preferred embodiment, the natural ligand is an agonist of the protein. In another embodiment, the natural ligand is an antagonist of the protein.

One embodiment of this invention relates to a method for identifying a compound capable of associating with a protein, wherein said protein has a natural ligand comprising at least one mechanistically significant phosphate group, said method comprising the steps of:

a.) selecting a first compound comprising a sulfhydantoin moiety or a reverse sulfhydantoin moiety; and b.) optionally modifying said first compound to optimize at least one additional structural feature for association with said protein.

According to a preferred embodiment, said optimization comprises optimizing structure-activity relationships. In a more preferred embodiment, said optimization comprises molecular modeling.

In another preferred embodiment, the protein is an enzyme. Preferably, the enzyme is a binding domain for the natural ligand. More preferably, the binding domain is a receptor for the natural ligand.

In a preferred embodiment, the natural ligand is a substrate of the protein. In another embodiment, the natural ligand is a second protein. In a preferred embodiment, the natural ligand is an agonist of the protein. In another embodiment, the natural ligand is an antagonist of the protein.

In a preferred embodiment, said compound is an inhibitor of the protein.

In another preferred embodiment, the protein is a phosphatase. More preferably, the compound is a phosphatase inhibitor.

In another preferred embodiment, the phosphatase is SHP-2. More preferably, the compound is an SHP-2 inhibitor.

One embodiment of this invention relates to a method for producing a compound capable of associating with a protein, wherein said protein has a natural ligand comprising at least one mechanistically significant phosphate group, said method comprising the step of replacing said phosphate group in said natural ligand with a sulfhydantoin moiety or a reverse sulfhydantoin moiety to produce said compound.

In a preferred embodiment, the protein is an enzyme. Preferably, the enzyme is a binding domain for the natural ligand. More preferably, the binding domain is a receptor for the natural ligand.

In a preferred embodiment, the natural ligand is a substrate of the protein. In another embodiment, the natural ligand is a second protein. In a preferred embodiment, the natural ligand is an agonist of the protein. In another embodiment, the natural ligand is an antagonist of the protein.

In a preferred embodiment, said compound is an inhibitor of the protein.

In another preferred embodiment, the protein is a phosphatase. More preferably, the compound is a phosphatase inhibitor.

In another preferred embodiment, the phosphatase is SHP-2. More preferably, the compound is an SHP-2 inhibitor.

One embodiment of this invention relates to a protein: ligand complex wherein the ligand is a compound according to formula I.

In a preferred embodiment, the protein is an enzyme. Preferably, the enzyme is a binding domain for the natural ligand. More preferably, the binding domain is a receptor for the natural ligand.

In another preferred embodiment, the protein is a phosphatase. More preferably, the phosphatase is SHP-2.

In a preferred embodiment, the compound is a substrate of the protein. In another embodiment, the compound is an inhibitor of the protein. In a preferred embodiment, the compound is an agonist of the protein. In another embodiment, the compound is an antagonist of the protein.

Without wishing to be bound by theory, applicants believe that the sulfhydantoin and reverse sulfhydantoin moieties described herein have the same shape as a phosphate group, as could be demonstrated, for example, by the overlap of the molecular model of a sulfhydantoin moiety with the molecular model of a phosphate group. Based on this similarity in shape, the sulfhydantoin and reverse sulfhydantoin moieties of the present invention are expected to bind in a fashion similar to that of the phosphate group. In addition, the sulfhydantoin and reverse sulfhydantoin moieties described herein may be useful as covalent, irreversible inhibitors of enzymes such as phosphatase enzymes, and could serve, for example, as probes in obtaining crystallographic data.

One embodiment of this invention relates to the use of a sulfhydantoin moiety or a reverse sulfhydantoin moiety as a phosphate isostere. One of ordinary skill in the art will appreciate that there are a number of means to design the phosphate isosteres of the present invention. These same means may be used to select a compound for screening as a ligand of a protein that has a natural ligand comprising at least one mechanistically significant phosphate group. This design or selection may begin with selection of the various moieties that fill the phosphate group binding pocket.

There are a number of ways to select moieties to fill individual phosphate group binding pockets. These include visual inspection of a physical model or computer model of the phosphate group binding pocket and manual docking of models of selected moieties into various phosphate group binding pockets. Modeling software that is well known and available in the art may be used. This includes QUANTA (Molecular Simulations, Inc., Burlington, Mass., 1992), SYBYL (Molecular Modeling Software, Tripos Associates, Inc., St. Louis, Mo., 1992), AMBER (Weiner et al., *J. Am. Chem. Soc.* (1984) 106, 765-784), or CHARMM (Brooks et al., *J. Comp. Chem.* (1983) 4, 187-217). This modeling step may be followed by energy minimization with standard molecular mechanics forcefields such as CHARMM and AMBER. In addition, there are a number of more specialized computer programs to assist in the process of selecting the binding moieties of this invention. These include:

1. GRID (Goodford, A Computational Procedure for Determining Energetically Favorable Binding Sites on Biologically Important Macromolecules, *J. Med. Chem.* (1985) 28, 849-857). GRID is available from Oxford University, Oxford, UK.
2. 3D Database systems such as MACCS-3D (MDL Information Systems, San Leandro, Calif.). This area has been reviewed by Martin (Martin, 3D Database Searching in Drug Design, *J. Med. Chem.* (1992) 35, 2145-2154).
3. HOOK (available from Molecular Simulations, Burlington, Mass.).

In addition to the above computer-assisted modeling of phosphate isosteres, the phosphate isosteres of this invention may be constructed "de novo" using either an empty active site or binding pocket of a protein, or optionally including some portions of a known inhibitor of a protein. Such methods are well known in the art. They include, for example:

1. LUDI (Bohm, The Computer Program LUDI: A New Method for the De Novo Design of Enzyme Inhibitors, *J. Comp. Aid. Molec. Design.* (1992) 6, 61-78). LUDI is available from Biosym Technologies, San Diego, Calif.
2. LEGEND (Nishibata et al., *Tetrahedron* (1991) 47, 8985). LEGEND is availabe from Molecular Simulations, Burlington, Mass.
3. LeapFrog (available from Tripos associates, St. Louis, Mo.).

A number of techniques commonly used for modeling drugs may be employed. For a review, see Cohen et al., Molecular Modeling Software and Methods for Medicinal Chemistry, *J. Med. Chem.* (1990) 33, 883-894. There are likewise a number of examples in the chemical literature of techniques that can be applied to specific drug design projects. For a review, see Navia et al., The Use of Structural Information in Drug Design, *Current Opinions in Structural Biology* (1992) 2, 202-210.

A variety of conventional techniques may be used to carry out each of the above evaluations as well as the evaluations necessary in screening a compound for phosphatase inhibitory activity. Generally, these techniques involve determining the location and binding proximity of a given moiety, the occupied space of a bound ligand, the deformation energy of binding of a given compound and electrostatic interaction energies. Examples of conventional techniques useful in the above evaluations include: quantum mechanics, molecular mechanics, molecular dynamics, Monte Carlo sampling, systematic searches, and distance geometry methods (Marshall, *Ann. Ref. Pharmacol. Toxicol.* (1987) 27, 193). Specific computer software has been developed for use in carrying out these methods. Examples of programs designed for such uses include: Gaussian 92, revision E.2 (Frisch, Gaussian, Inc., Pittsburgh, Pa. (c) 1993); AMBER, version 4.0 (P.A. Kollman, University of California at San Francisco (c) 1993); QUANTA/CHARMM (Molecular Simulations, Inc., Burlington, Mass. (c) 1992); and Insight II/Discover (Biosysm Technologies Inc., San Diego, Calif. (c) 1992). These programs may be implemented, for instance, using a Silicon Graphics Indigo 2 workstation or IBM RISC/6000 workstation model 550. Other hardware systems and software packages will be known and of evident applicability to those skilled in the art.

One embodiment of the present invention relates to compounds of formulae (I) and (II) wherein the radical Q is attached to the sulfhydantoin or reverse sulfhydantoin core directly (I-A and II-A); via —$CH_2$-(I-B and II-B); or via —C(O)NH—($C_{1-6}$ alkylidene)— (I-C and II-C); as shown below:

(I-A)

(II-A)

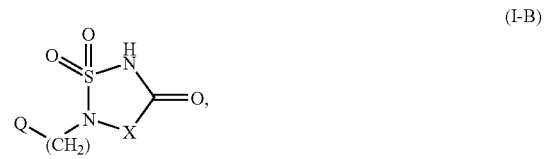

(I-B)

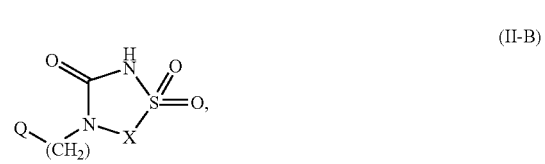

(II-B)

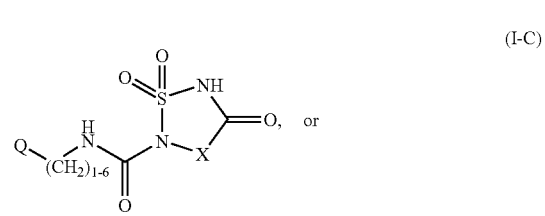

(I-C)

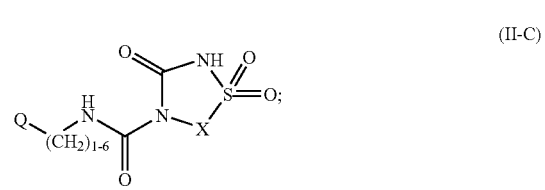

(II-C)

wherein X and Q are as described above.

Preferred Q groups of formulae I or II, or of any of subformulae I-A, II-A, I-B, II-B, I-C, or II-C are optionally substituted groups selected from: $C_{6-10}$ aryl and 5-6 membered heterocyclyl.

According to a preferred embodiment, in compounds of formulae I or II, or of any of subformulae I-A, II-A, I-B, II-B, I-C, or II-C, X is —$CH_2$—.

Preferred compounds of formula I are set forth in Table 1 below.

TABLE 1
Compounds of Formula I
| No. | —X— | —T$_m$Q |
|---|---|---|
| I-1 | —CH$_2$— | 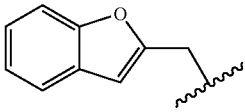 |
| I-2 | —CH$_2$— | 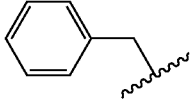 |
| I-3 | —CH$_2$— | 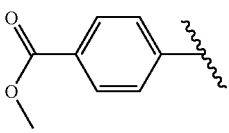 |
| I-4 | —CH$_2$— | 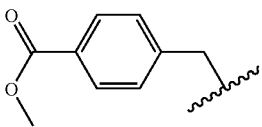 |
| I-5 | —CH$_2$— | 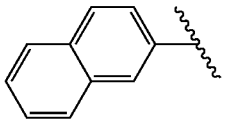 |
| I-6 | —CH$_2$— | 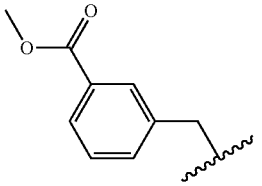 |
| I-7 | —CH$_2$— | 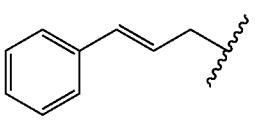 |
TABLE 1-continued
Compounds of Formula I
| No. | —X— | —T$_m$Q |
|---|---|---|
| I-8 | —CH$_2$— | 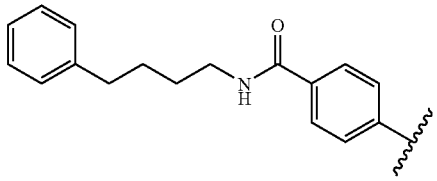 |
| I-9 | —CH$_2$— | 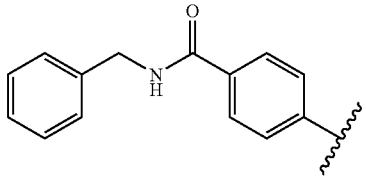 |
| I-10 | —CH$_2$— | 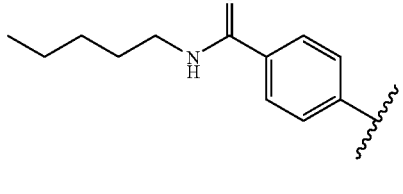 |
| I-11 | —CH$_2$— | 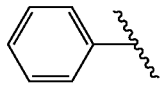 |
| I-12 | —CH$_2$— | 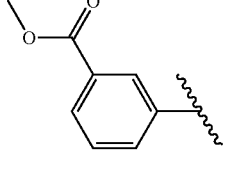 |
| I-13 | —CH$_2$— | 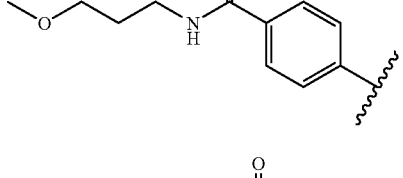 |
| I-14 | —CH$_2$— | 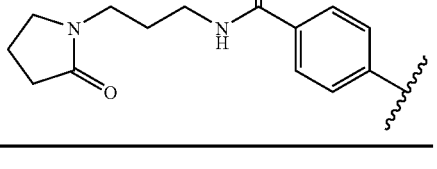 |
The present compounds may be prepared in general by methods known to those skilled in the art for analogous compounds, as illustrated by the Schemes and synthetic Examples shown below.

Scheme 3

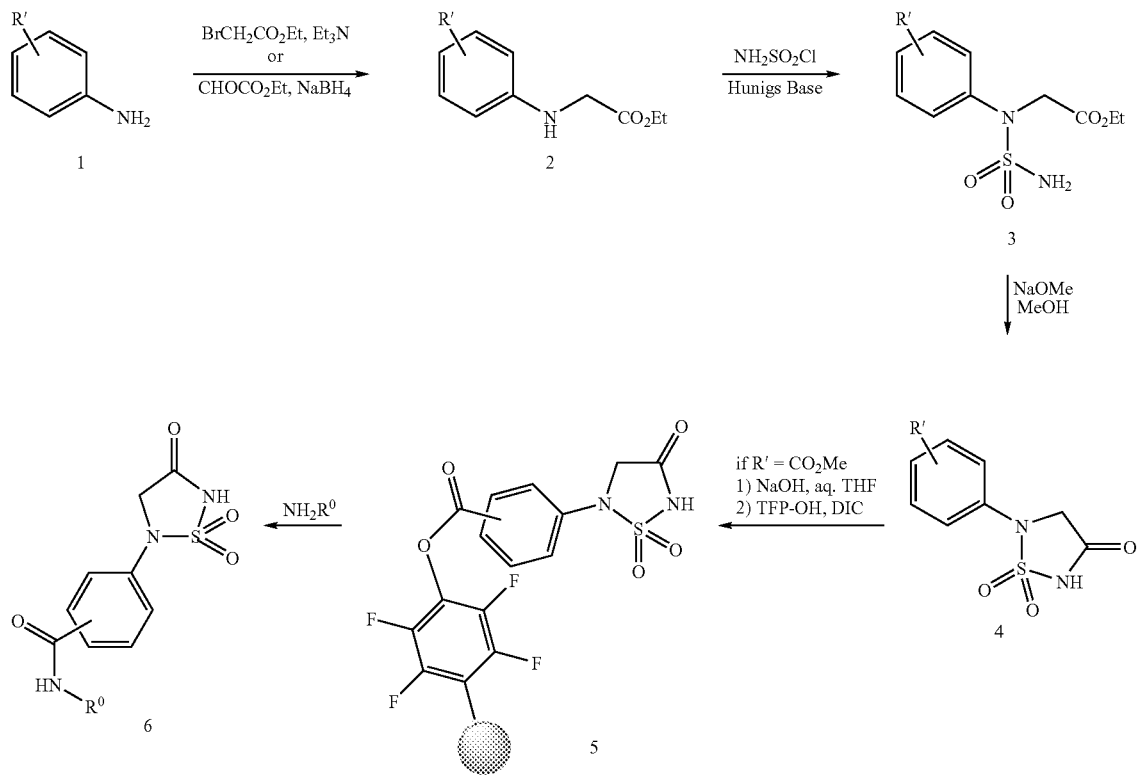

Scheme 3 shows a general method for the preparation of compounds of formula I, wherein m is zero and Q is a substituted phenyl ring. Anilines 1 may be alkylated to form amines 2. Amines 2 may then be coupled with a sulfamyl chloride (formed by the addition of formic acid to chlorosulfonyl isocyanate) to provide sulfonamides 3 (Albericio et al., J. Combi. Chem. (2001) 3, 290). Cyclization may then be effected to form sulfhydantoins 4, which may be further derivatized as required through methods known in the art. It will be obvious to one of skill in the art that other aniline derivatives may be used to provide other compounds according to the present invention.

Scheme 4

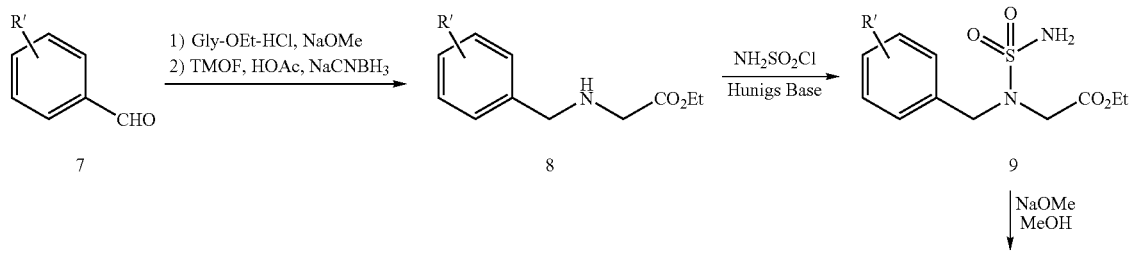

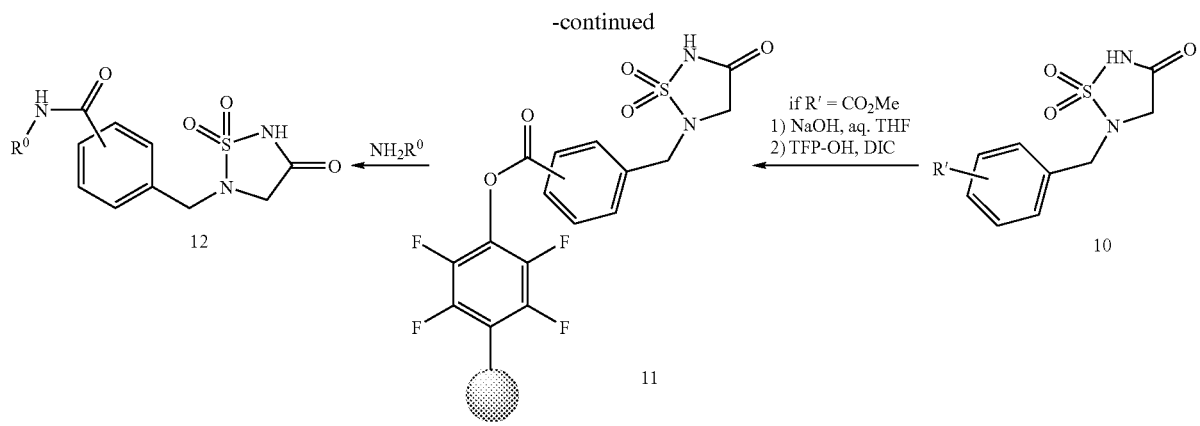

Scheme 4 shows another general method for the preparation of compounds of formula I, wherein $T_m$ is —$CH_2$— and Q is a substituted phenyl ring. The —$CH_2$— linker is provided by reductive amination of aldehydes 7 to form amines 8 (Grundke, *Synthesis* (1987) 1115), which may then be further derivatized as set forth in Scheme 3 above.

The activity of a compound utilized in this invention as an inhibitor of SHP-2 phosphatase may be assayed in vitro, in vivo or in a cell line according to methods known in the art. In vitro assays include assays that determine inhibition of phosphorylation by SHP-2. In vitro assays quantitate the ability of the inhibitor to bind to SHP-2. Inhibitor binding may be measured by radiolabelling the inhibitor prior to binding, isolating the inhibitor/SHP-2 complex and determining the amount of radiolabel bound. Alternatively, inhibitor binding may be determined by running a competition experiment where new inhibitors are incubated with SHP-2 bound to known radioligands. Detailed conditions for assaying a compound utilized in this invention as an inhibitor of SHP-2 are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably modulate a phosphatase enzyme, particularly SHP-2, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants, or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The term "detectably modulate", as used herein means a measurable change in phosphatase activity between a sample comprising said composition and phosphatase enzyme and an equivalent sample comprising phosphatase enzyme in the absence of said composition.

A "pharmaceutically acceptable derivative" means any non-toxic salt, ester, salt of an ester, or other derivative of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium, and $N^+$ ($C_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed, including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers that are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax, and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax, and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

For ophthalmic use, the pharmaceutically acceptable compositions may be formulated as micronized suspensions in isotonic, pH-adjusted sterile saline, or, preferably, as solutions in isotonic, pH-adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated and the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed; the age, body weight, general health, sex and diet of the patient; the time of administration; the rate of excretion; the drug combination; the judgment of the treating physician; and the severity of the particular disease being treated. The amount of a compound of the present invention in the composition will also depend upon the particular compound in the composition.

Depending upon the particular condition or disease to be treated or prevented, additional therapeutic agents, which are normally administered to treat or prevent that condition in a monotherapy, may also be present in the compositions of this invention.

For example, chemotherapeutic agents or other anti-proliferative agents may be combined with the compounds of this invention to treat cancer and proliferative diseases. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents with which the compounds of this invention may be combined include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti- Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting phosphatase activity in a biological sample comprising the step of contacting said biological sample with a compound of this invention, or a composition comprising said compound. According to a preferred embodiment, the invention relates to a method of inhibiting SHP-2 activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of SHP-2 activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of a disease selected from autoimmune diseases, proliferative diseases, angiogenic disorders, and cancers.

According to a preferred embodiment, the invention provides a method for treating or lessening the severity of a SHP-2-mediated disease or condition in a patient comprising the step of administering to said patient a composition according to the present invention.

The term "SHP-2-mediated disease," as used herein means any disease or other deleterious condition in which SHP-2 is known to play a role. Such conditions include, without limitation, autoimmune diseases, proliferative diseases, angiogenic disorders, and cancers.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma, and HTLV-1-mediated tumorigenesis.

Angiogenic disorders that may be treated or prevented by the compounds of this invention include solid tumors, ocular neovasculization, and infantile haemangiomas.

Cancers that may be treated or prevented by the compounds of this invention include, without limitation, colon, breast, stomach, and ovarian cancers.

In another embodiment, the methods of this invention that utilize compositions that do not contain an additional therapeutic agent, comprise the additional step of separately administering to said patient an additional therapeutic agent. When these additional therapeutic agents are administered separately, they may be administered to the patient prior to, sequentially with, or following administration of the compositions of this invention.

The compounds of this invention or pharmaceutical compositions thereof may also be incorporated into compositions for coating an implantable medical device, such as prostheses, artificial valves, vascular grafts, stents, and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by a suitable topcoat of fluorosilicone, polysaccarides, polyethylene glycol, phospholipids, or combinations thereof to impart controlled-release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXAMPLES

Example 1

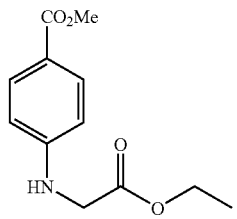

101

4-(Ethoxycarbonylmethylamino)-benzoic acid methyl ester (101): A solution of aniline, triethyl amine, and ethyl bromoacetate was heated to 60° C. for 2.5 days. The reaction mixture was cooled, and TLC (25% EtOAc/hex) showed mostly starting material and a higher $R_f$ spot. Additional base, bromide, and continued heat for 2 days brought little change by TLC. The reaction mixture was cooled, diluted with ethyl acetate, extracted with 10% HCl, dried over sodium sulfate, filtered, adsorbed onto silica, and purified by flash column using 10-30% ethyl acetate/hexanes to obtain 101 as a white solid.

Example 2

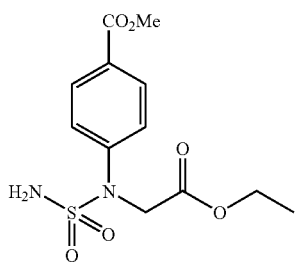

102

4-(Ethoxycarbonylmethylsulfamylamino)-benzoic acid methyl ester (102): A flame-dried flask was charged with chlorosulfonyl isocyanate. Anhydrous formic acid (96%) was added dropwise resulting in evolution of a gas. The solution solidified halfway through the addition of the formic acid and eventually turned to a cloudy liquid (the crude sulfamyl chloride). The solution was stirred at room temperature until no further gas evolution was observed. The sulfonyl chloride was diluted with 20 mL dry methylene chloride and added to a 0° C. solution of 101/triethyl amine in 20 mL methylene chloride. The reaction was stirred from 0° C. to room temperature over 2 hours (TLC showed approximately 50% starting material in 30% ethyl acetate/hexanes) and overnight at room temperature. The reaction showed mostly two spots by TLC (70:30 ethyl acetate:hexanes). The reaction was diluted with methylene chloride, washed with 10% HCl, dried over sodium sulfate, filtered, and concentrated to a light yellow oil. The crude mixture was purified by flash column by adsorbing onto silica and eluting with 20% ethyl acetate/hexanes to recover starting material and the white solid 102.

Example 3

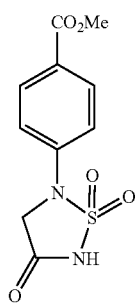

103

4-(1,1,4-Trioxo-1λ$^6$-[1,2,5]thiadiazolidin-2-yl)-benzoic acid methyl ester (103): Compound 102 was dissolved in 5 mL of methanol and cooled to 0° C. A solution of freshly prepared NaOMe in methanol was added, and the solution was warmed to room temperature and stirred overnight. TLC (70:30 hexanes/ethyl acetate) showed no starting material. The reaction was acidified with Dowex resin, filtered, and concentrated to a white solid. The compound 103 was recrystallized from ethyl acetate/hexanes.

Example 4

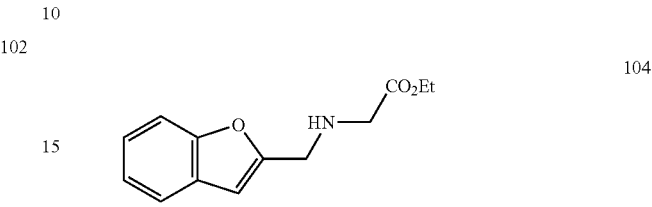

104

[(Benzofuran-2-ylmethyl)-amino]-acetic acid ethyl ester (104): Glycine ethyl ester hydrochloride was dissolved in 100 mL dry methanol. Sodium carbonate was added, followed by benzofuran-2-carbaldehyde and about 10 grams of sodium sulfate. The reaction was stirred at room temperature for 12 hours. The reaction was filtered and the mother liquor concentrated. The residue was resuspended in THF and filtered again. To the filtrate was added sodium triacetoxy borohydride, and the reaction was stirred at room temperature for 12 hours to afford a cloudy solution. 1N NaOH was added, and the solution became clear. The reaction was poured into ethyl acetate, washed with brine, dried over sodium sulfate, filtered, and concentrated to a thick yellow oil. The oil was purified by column chromatography using 10-30% ethyl acetate/hexanes to obtain two viscous yellow oils. The less polar oil appeared to contain mostly the corresponding imine. The more polar oil was the desired product 104.

Example 5

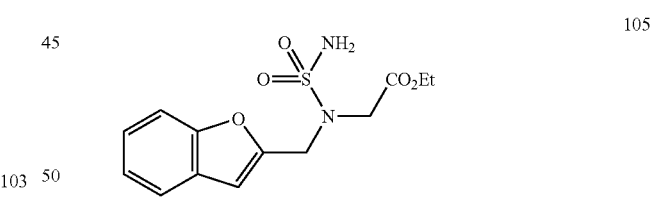

105

[(Benzofuran-2-ylmethyl)-sulfamylamino]-acetic acid ethyl ester (105): A stock of sulfamyl chloride was prepared by adding formic acid to chlorosulfonyl isocyanate. The sulfamyl chloride was added to a room temperature solution of 104 and triethyl amine in methylene chloride. The reaction was stirred at room temperature overnight. TLC (30% ethyl acetate/hexanes) showed a major spot and a minor product. The reaction was poured into 10% HCl, extracted with methylene chloride, dried over sodium sulfate, filtered, and concentrated to a thick yellow syrup. The crude syrup was adsorbed onto silica and purified by flash chromatography with 15-30% ethyl acetate/hexanes to obtain the final product 105 as a light yellow film.

Example 6

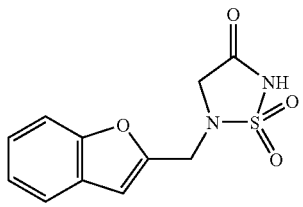

5-Benzofuran-2-ylmethyl-1,1-dioxo-$\lambda^6$-[1,2,5]thiadiazolidin-3-one (106): 105 was dissolved in 10 mL dry methanol at room temperature. NaOMe solution was added dropwise, and the reaction was stirred at room temperature for two hours. No precipitate formed, although TLC (30% ethyl acetate/hexanes) showed no starting material. Dowex resin was added, the solution was stirred for 20 minutes, and then filtered and concentrated to a yellow film. The film was taken up in ethyl acetate, and a precipitate formed. The solid 106 was collected by filtration and washed with hexanes. The washings were also collected and concentrated to provide additional product.

Example 7

SHP-2 Assay

N-terminal 6 His-tagged, catalytic domain of SHP-2 (250-527) was expressed in *E. coli*, and the protein was purified by conventional methods. SHP-2 activity was assessed by measuring the fluorescent signal generated by the dephosphorylation of fluorescein diphosphate (FDP) by SHP-2. The assay was carried out in 96-well polypropylene block plates. The final assay volume was 100 μL and comprised 25 mM NaOAc, pH 6, 0.02% Triton X-100, 10 mM DTT, and 2 nM SHP-2. Inhibitors were suspended in DMSO, and all reactions including controls were performed at a final concentration of 3% DMSO. Reactions were initiated by the addition of 3 μM FDP and incubated at ambient temperature for 45 minutes. Plates were read using a Molecular Devices Gemini plate reader, Ex 485, Em 538, Cutoff 530.

Results for the SHP-2 assay for the compounds of this invention are shown in Table 2 below:

| Compound | SHP-2 IC$_{50}$ |
|---|---|
| I-1 | ++ |
| I-2 | ++ |
| I-3 | ++ |
| I-4 | + |
| I-5 | + |
| I-6 | + |
| I-7 | + |
| I-8 | + |
| I-9 | + |
| I-10 | + |

For SHP-2 IC$_{50}$ values, "+++" represents <1.0 μM, "++" represents between 1.0 and 100 μM, and "+" represents >100 μM.

While we have presented a number of embodiments of this invention, it is apparent that our basic construction can be altered to provide other embodiments that utilize the compounds and methods of this invention. Therefore, it will be appreciated that the scope of this invention is to be defined by the appended claims rather than by the specific examples which have been provided herewith by way of example.

The invention claimed is:

1. A compound selected from:

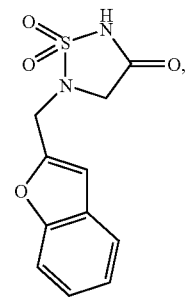

I-1

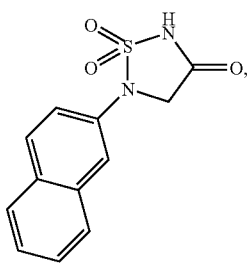

I-5

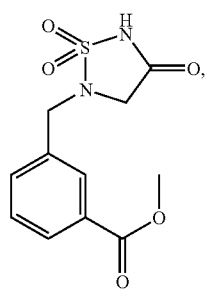

I-6

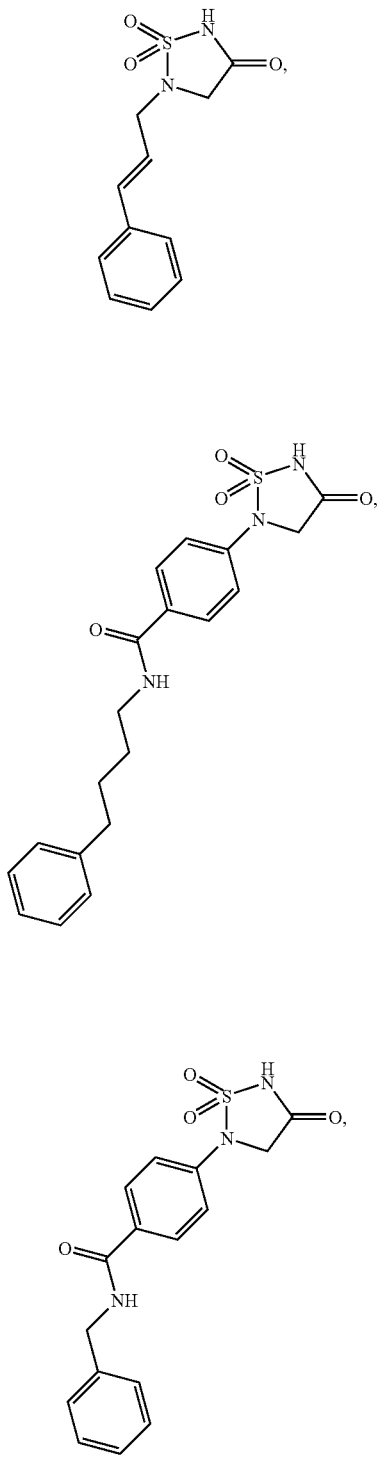
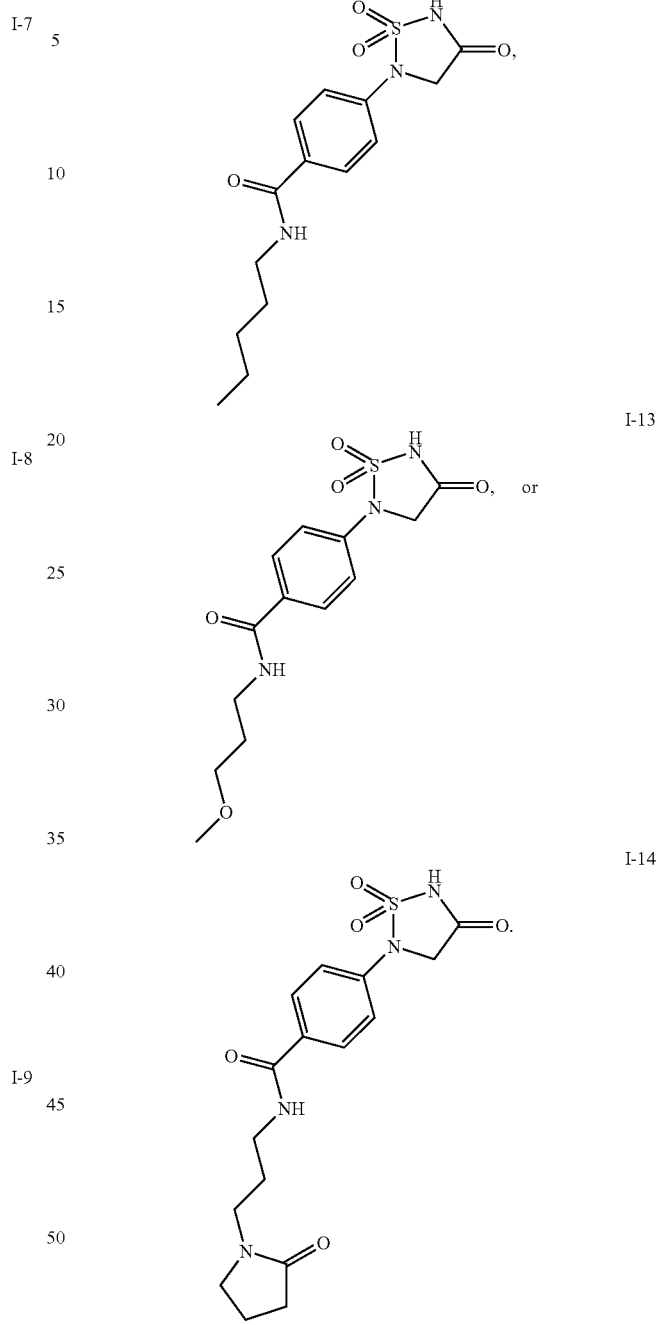
2. A pharmaceutical composition comprising a compound according to claim 1 and a pharmaceutically acceptable carrier, adjuvant, or vehicle.
3. The composition according to claim 2 wherein the composition comprises an additional therapeutic agent.
* * * * *